US009820716B2

(12) United States Patent
Baba et al.

(10) Patent No.: US 9,820,716 B2
(45) Date of Patent: Nov. 21, 2017

(54) ULTRASONIC IMAGING APPARATUS AND A METHOD FOR GENERATING AN ULTRASONIC IMAGE (75) Inventors: Tatsuro Baba, Otawara (JP); Naohisa Kamiyama, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 1718 days.

(21) Appl. No.: 12/238,829

(22) Filed: Sep. 26, 2008

(65) Prior Publication Data

US 2009/0088641 A1   Apr. 2, 2009

(30) Foreign Application Priority Data

Sep. 28, 2007   (JP) ................................ 2007-254337

(51) Int. Cl.
*A61B 8/06* (2006.01)
*A61B 8/00* (2006.01)
*G01S 7/52* (2006.01)
*G01S 15/58* (2006.01)

(52) U.S. Cl.
CPC ................ *A61B 8/06* (2013.01); *A61B 8/469* (2013.01); *G01S 7/52034* (2013.01); *G01S 7/52066* (2013.01); *G01S 7/52063* (2013.01); *G01S 15/584* (2013.01)

(58) Field of Classification Search
CPC .. A61B 8/00; A61B 8/06; A61B 8/488; A61B 8/463; A61B 8/54; A61B 8/5207; A61B 8/065; A61B 8/469; G01S 7/52066; G01S 7/5205; G01S 7/52073; G06F 19/324; G06F 19/3437; G06F 19/321; G06F 19/3406
See application file for complete search history.

(56) References Cited

U.S. PATENT DOCUMENTS

| | | | |
|---|---|---|---|
| 6,663,566 B2 * | 12/2003 | Pan et al. | 600/454 |
| 6,733,454 B1 * | 5/2004 | Bakircioglu et al. | 600/453 |
| 2002/0116141 A1 * | 8/2002 | Mo et al. | 702/76 |

(Continued)

OTHER PUBLICATIONS

U.S. Appl. No. 12/140,607, filed Jun. 17, 2008, Tatsuro Baba, et al.

*Primary Examiner* — Katherine Fernandez
*Assistant Examiner* — Katherine McDonald
(74) *Attorney, Agent, or Firm* — Oblon, McClelland, Maier & Neustadt, L.L.P.

(57) ABSTRACT

A scanner transmits and receives ultrasonic waves at a specified pulse repetition frequency (PRF). A storage stores received signals acquired through the transmission and reception. A calculator generates a Doppler spectrum image by executing frequency analysis on the received signals. A display displays the Doppler spectrum image. When a desired Doppler velocity range for the displayed Doppler spectrum image is inputted, a processor reads out the received signals from the storage, and executes a resampling process on the read-out received signals at a sampling frequency corresponding to the desired Doppler velocity range. The calculator generates a new Doppler spectrum image by executing frequency analysis corresponding to the desired Doppler velocity range on the received signals having been subjected to the resampling process by the processor. The display displays the new Doppler spectrum image.

12 Claims, 7 Drawing Sheets (56) References Cited

U.S. PATENT DOCUMENTS

| | | | |
|---|---|---|---|
| 2003/0013959 A1* | 1/2003 | Grunwald et al. | 600/437 |
| 2004/0254439 A1* | 12/2004 | Fowkes | A61B 8/00 600/407 |
| 2004/0254467 A1* | 12/2004 | Jackson | 600/450 |
| 2006/0052704 A1 | 3/2006 | Baba et al. | |
| 2006/0058662 A1* | 3/2006 | Kobayashi et al. | 600/437 |
| 2007/0167790 A1* | 7/2007 | Kim et al. | 600/454 |
| 2007/0282203 A1* | 12/2007 | Baba et al. | 600/453 |
| 2008/0114240 A1* | 5/2008 | Sasaki | 600/440 |
| 2008/0228078 A1* | 9/2008 | Kim et al. | 600/453 |

* cited by examiner

ULTRASONIC IMAGING APPARATUS AND A METHOD FOR GENERATING AN ULTRASONIC IMAGE

BACKGROUND OF THE INVENTION

1. Field of the Invention

The present invention relates to an ultrasonic imaging apparatus configured to acquire a Doppler spectrum image by transmitting and receiving ultrasonic waves to and from a subject and adjust the Doppler velocity range of the Doppler spectrum image, and also relates to a method for generating an ultrasonic image.

2. Description of the Related Art

An ultrasonic imaging apparatus that obtains blood-flow information of a diagnosis site by the ultrasonic Doppler method is known. The ultrasonic Doppler method is a technique of obtaining information on the blood flow in a subject based on the principles of the ultrasonic Doppler method. When ultrasonic waves are transmitted to a diagnosis site having a stream like a blood flow in a subject, the reception frequency slightly shifts from the transmission frequency by the Doppler Effect. This shift frequency (Doppler shift frequency) is proportional to a blood-flow velocity. Blood-flow information is obtained by frequency analysis of the Doppler shift frequency.

The ultrasonic imaging apparatus executes Fast Fourier Transform (FFT) on an obtained Doppler signal. Then, the ultrasonic imaging apparatus displays the spectrum of the result of the frequency analysis, taking frequency f (velocity v) on the vertical axis and time t on the horizontal axis. Measurement of various kinds of items used in diagnosis is executed on the spectrum image.

In a Doppler spectrum image acquired by the pulsed wave Doppler method (PWD), a phenomenon of aliasing (folding) occurs when a sampling frequency fs for the frequency analysis is lower than the Doppler shift frequency. In order to prevent this phenomenon, it is necessary to raise the pulse repetition frequency (PRF), which corresponds to the sampling frequency, and to shorten each interval of observation times. When a position desired to measure is designated, the maximum value of the PRF is necessarily determined. When the PRF is determined, the maximum blood-flow velocity that can be measured is also determined. This maximum blood-flow velocity that can be measured is referred to as the "Doppler velocity range."

At the time of Doppler spectrum display, a folding portion is generated in a Doppler waveform when the Doppler velocity range is too small. In this case, the operator manually sets a larger Doppler velocity range, with the result that the folding portion falls within a nyquist frequency (half of the PRF), and a smooth continuous Doppler spectrum is obtained in the display. On the contrary, when the Doppler velocity range is too large, the scale of the display is large and the Doppler waveform is displayed small. Such a Doppler waveform displayed small makes observation difficult. In this case, the operator manually sets a smaller Doppler velocity range, with the result that it is possible to display the Doppler spectrum over the full height of a display screen. Besides, it is possible to display the Doppler waveform at a desired position of the Doppler velocity range (vertical axis) by adjusting velocity offset, namely, baseline shift (BLS).

Since the blood-flow velocity varies depending on patients and diagnosis sites, the acquired Doppler waveform also varies depending on patients and diagnosis sites. Therefore, it is necessary to set the Doppler velocity range in accordance with the Doppler waveform. To be specific, the operator needs to adjust the pulse repetition frequency (PRF) corresponding to the Doppler velocity range and the velocity offset (BLS), for each patient and diagnosis site. However, it is cumbersome to adjust the Doppler velocity range (PRF) and the velocity offset (BLS) for each patient and diagnosis site.

Therefore, a technique of automatically determining the Doppler velocity range (PRF) and the velocity offset (BLS) is proposed (for example, Japanese Unexamined Patent Application Publication JP-A 2005-185731).

Conventionally, the Doppler velocity range (PRF) and the velocity offset (BLS) are obtained by assessing past blood-flow conditions and feeding back the result of the assessment. Then, the Doppler velocity range and the velocity offset are tracked in real time by assessing the blood-flow conditions in real time.

However, there is a problem such that a time lag arises because the Doppler velocity range (PRF) and the velocity offset (BLS) are estimated by assessing the past blood-flow conditions. Moreover, the past blood-flow conditions do not necessarily coincide with present and later blood-flow conditions. Therefore, it is difficult to obtain a Doppler velocity range and a velocity offset that are suitable for a Doppler waveform acquired now and later.

Further, conventionally, the operator gives a trigger at a time point when the blood-flow conditions become stable, and after that, the Doppler velocity range (PRF) and the velocity offset (BLS) are estimated. However, when a variation such as breathing of a subject and displacement of an ultrasonic probe occurs after the operator gives the trigger, it is impossible to obtain the Doppler velocity range and velocity offset suitable for the Doppler waveform, and it is necessary to execute the estimation process again.

SUMMARY OF THE INVENTION

An object of the present invention is to provide an ultrasonic imaging apparatus capable of displaying a Doppler spectrum image with a desired Doppler velocity range, and also provide a method for generating the Doppler spectrum image.

In a first aspect of the present invention, an ultrasonic imaging apparatus comprises: a scanner configured to transmit and receive ultrasonic waves to and from a diagnosis site including a moving fluid in a subject at a specified pulse repetition frequency (PRF); a storage configured to store received signals acquired by the scanner; a calculator configured to generate a Doppler spectrum image by executing frequency analysis on the received signals; a display controller configured to control a display to display the Doppler spectrum image; an input part for designating a desired Doppler velocity range on the Doppler spectrum image displayed on the display; and a processor configured to receive the desired Doppler velocity range inputted from the input part, read out the received signals from the storage, and execute a resampling process on the read-out received signals at a sampling frequency corresponding to the desired Doppler velocity range. The calculator generates a new Doppler spectrum image by executing frequency analysis corresponding to the desired Doppler velocity range on the received signals having been subjected to the resampling process by the processor, and the display controller controls the display to display the new Doppler spectrum image.

In the first aspect of the present invention, a desired Doppler velocity range is designated on the Doppler spectrum image displayed on the display, and a resampling process and frequency analysis are executed on the received signals stored in the storage in accordance with the sampling frequency corresponding to the designated Doppler velocity range. Consequently, it becomes possible to display a Doppler spectrum image with a desired Doppler velocity range without deteriorating the temporal resolution and frequency decomposition.

In a second aspect of the present invention, a method for generating an ultrasonic image comprises: transmitting and receiving ultrasonic waves to and from a diagnosis site including a moving fluid in a subject at a specified pulse repetition frequency (PRF); storing received signals acquired in the transmission and reception into a storage; generating a Doppler spectrum image by executing frequency analysis on the received signals; displaying the Doppler spectrum image; when a desired Doppler velocity range is designated on the displayed Doppler spectrum image, reading out the received signals from the storage and executing a resampling process on the read-out received signals at a sampling frequency corresponding to the desired Doppler velocity range; generating a new Doppler spectrum image by executing frequency analysis corresponding to the desired Doppler velocity range on the received signals having been subjected to the resampling process; and displaying the new Doppler spectrum image.

DETAILED DESCRIPTION OF THE EMBODIMENTS

Figure 1:
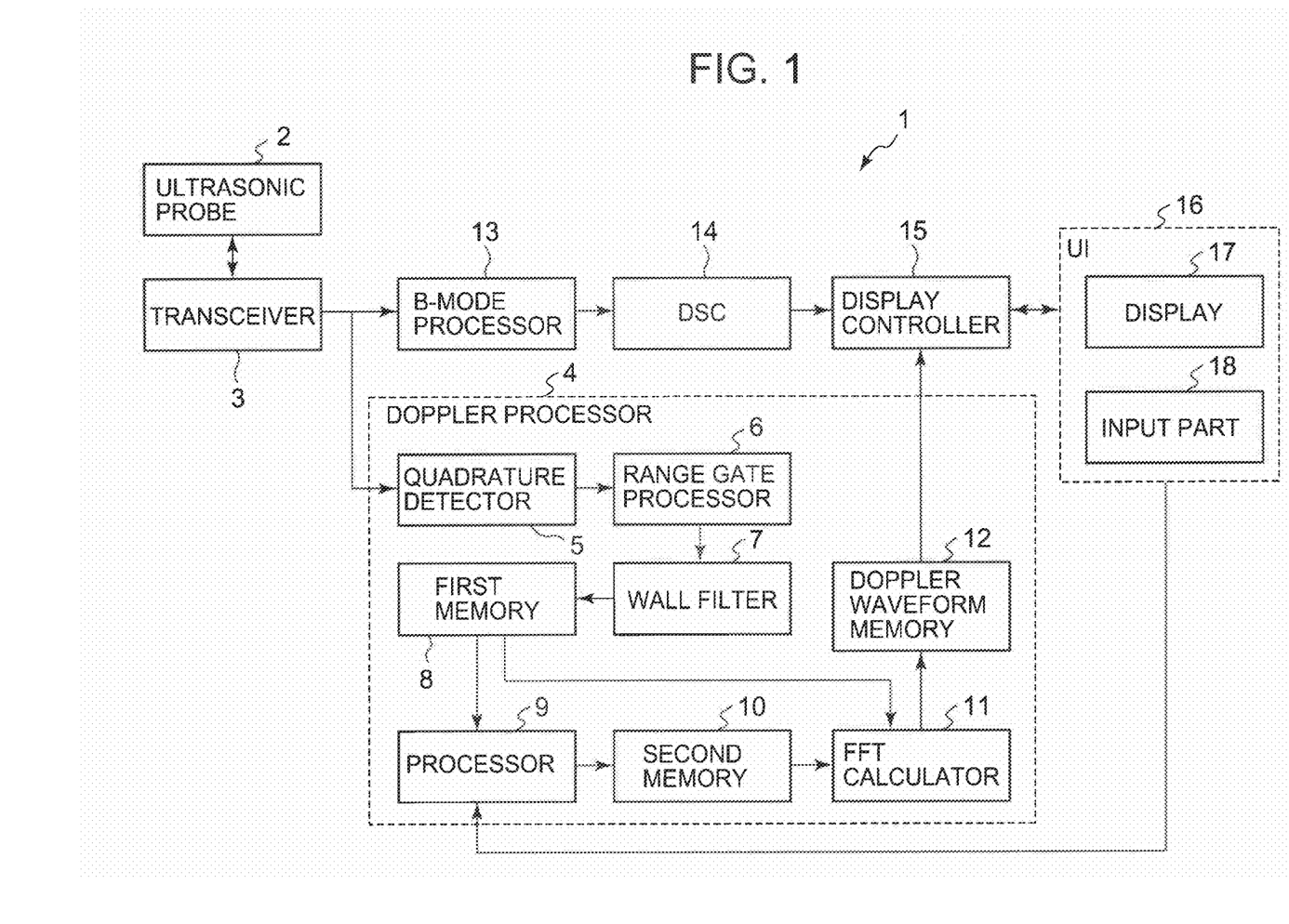
FIG. 1 is a block diagram showing an ultrasonic imaging apparatus according to an embodiment of the present invention.
Figure 2:
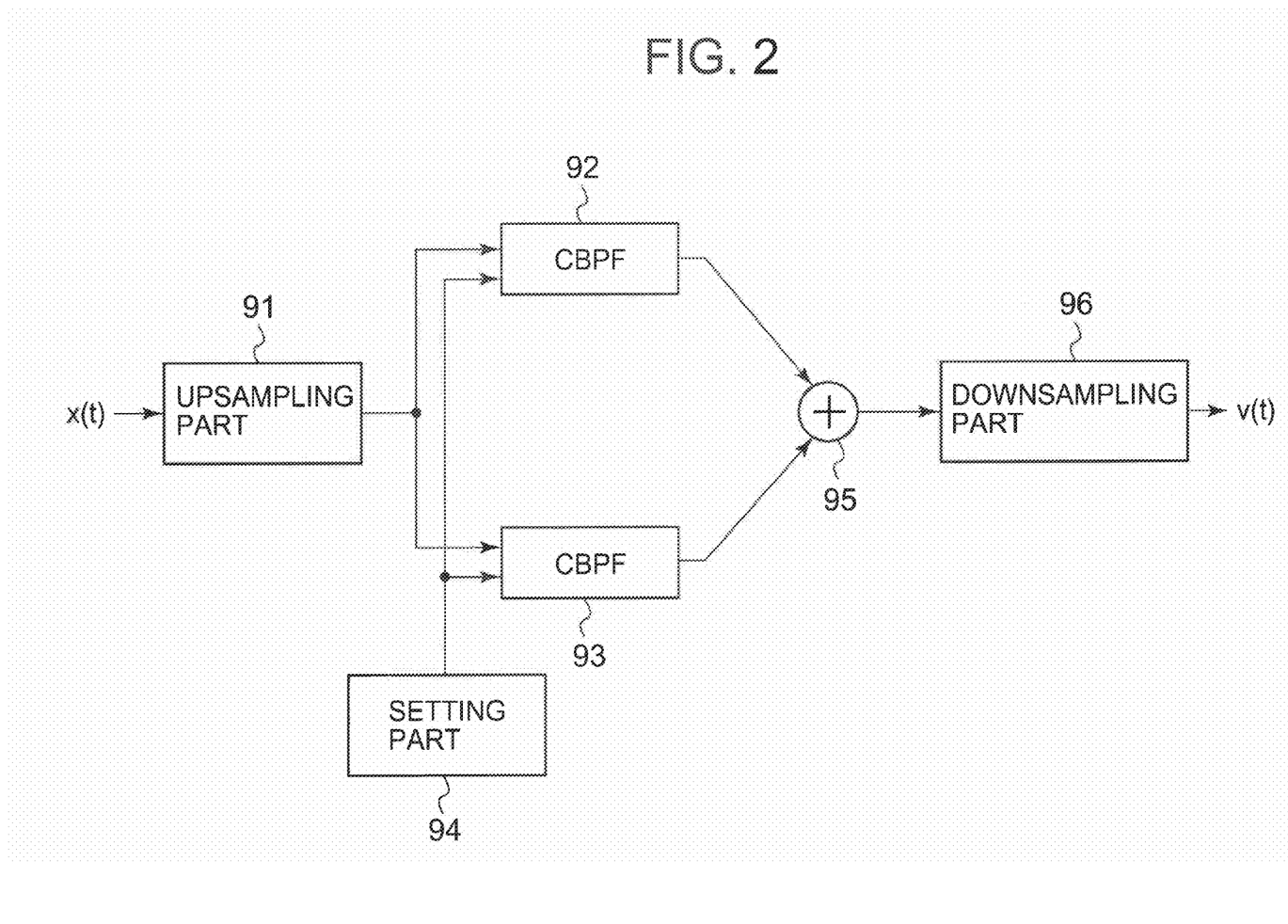
FIG. 2 is a block diagram showing a processor set in the ultrasonic imaging apparatus according to the embodiment of the present invention.

An ultrasonic imaging apparatus according to an embodiment of the present invention will be described with reference to FIG. 1 and FIG. 2. FIG. 1 is a block diagram showing the ultrasonic imaging apparatus according to the embodiment of the present invention. FIG. 2 is a block diagram showing a processor installed in the ultrasonic imaging apparatus according to the embodiment of the present invention.

An ultrasonic imaging apparatus 1 according to this embodiment comprises an ultrasonic probe 2, a transceiver 3, a Doppler processor 4, a B-mode processor 13, a DSC 14, a display controller 15, and a user interface (UI) 16. An ultrasonic image processing apparatus may be composed of the Doppler processor 4, the display controller 15 and the user interface (UI) 16.

As the ultrasonic probe 2, a 1D array probe with a plurality of ultrasonic transducers aligned in a specified direction (a scanning direction) is used. Alternatively, as the ultrasonic probe 2, a 2D array probe with a plurality of ultrasonic transducers arranged 2-dimensionally may be used.

The transceiver 3 includes a transmitter and a receiver. The transceiver 3 supplies electrical signals to the ultrasonic probe 2 and causes it to generate ultrasonic waves, and receives echo signals received by the ultrasonic probe 2.

The transmitter of the transceiver 3 includes a clock generation circuit, a transmission delay circuit, and a pulsar circuit, which are not shown. The clock generation circuit generates clock signals that determine the transmission timing and transmission frequency of ultrasonic signals. The transmission delay circuit executes transmission focus by applying a delay at the time of transmission of ultrasonic waves. The pulsar circuit has the same number of pulsars as that of individual channels for the respective ultrasonic transducers. The pulsar circuit generates a driving pulse at the delayed transmission timing and supplies electrical signals to the respective ultrasonic transducers of the ultrasonic probe 2. The transmitter of the transceiver 3 makes the ultrasonic probe 2 transmit ultrasonic waves at a specified pulse repetition frequency (PRF).

Further, the receiver of the transceiver 3 includes a preamplifier circuit, an A/D conversion circuit, a reception delay circuit, and an adder circuit, which are not shown. The preamplifier circuit amplifies echo signals outputted from the respective ultrasonic transducers of the ultrasonic probe 2 in the respective reception channels. The A/D conversion circuit executes A/D conversion on the amplified echo signals. The reception delay circuit applies a delay time necessary for determining the reception directionality of the echo signals after the A/D conversion. The adder circuit adds the delayed echo signals.

Through this addition, reflected components from the direction according to the reception directionality are emphasized. The signals having been subjected to the adding process by the transceiver 3 may be referred to as "RF signals." The transceiver 3 outputs the RF signals to the Doppler processor 4 or the B-mode processor 13.

The B-mode processor 13 images the amplitude information of the echoes and generates B-mode ultrasonic raster data from the echo signals. To be specific, the B-mode processor 13 executes a band pass filter process on the RF signals, and then detects the envelope curve of the outputted signals. The B-mode processor 13 then executes a compression process by logarithmic transformation on the detected data, thereby imaging the amplitude information of the echoes. The B-mode ultrasonic raster data generated by the B-mode processor 13 is outputted to the DSC 14.

The DSC (Digital Scan Converter) 14 converts the ultrasonic raster data into image data represented by the orthogonal coordinates in order to obtain an image represented by the orthogonal coordinates, which is referred to as a scan conversion process. The DSC 14 outputs the image data to the display controller 15. The display controller 15 controls a display 17 to display an image based on the image data. For example, the DSC 14 generates tomographic image data of 2-dimensional information based on the B-mode ultrasonic raster data, and outputs the tomographic image data to the display controller 15.

The display controller 15 controls the display 17 to display a tomographic image based on the tomographic image data.

The Doppler processor 4 includes a quadrature detector 5, a range gate (RG) processor 6, a wall filter 7, a first memory 8, a processor 9, a second memory 10, an FFT calculator 11, and a Doppler waveform memory 12.

The quadrature detector 5 includes a digital mixer and a low pass filter (LPF) so as to correspond to a real-part component and an imaginary-part component, respectively, and executes quadrature detection on the RF signals. The quadrature detector 5 then outputs a digital quantity of IQ signals having been subjected to the quadrature detection. Through this detection, baseband Doppler signals (real-part component and imaginary-part component: IQ signals) are extracted from the RF signals.

The range gate (RG) processor 6 receives the IQ signals outputted from the quadrature detector 5 and eliminates high-frequency components from the IQ signals, thereby obtaining Doppler signals composed of only Doppler shift frequency components. The range gate (RG) processor 6 then extracts Doppler signals at a desired depth in the subject from the Doppler signals composed of only Doppler shift frequency components.

The wall filter 7 eliminates unwanted low-frequency Doppler signals that represent a relatively slow-moving blood vessel wall, cardiac wall and the like from the Doppler signals (IQ signals) at the desired position in the subject designated by the range gate in the range gate processor 6. Thus, the wall filter 7 extracts Doppler signals (IQ signals) of a blood flow that should be detected. The IQ signals outputted from the wall filter 7 are then stored into the first memory 8.

The FFT calculator 11 executes frequency analysis on the Doppler signals (IQ signals) extracted by the wall filter 7 to obtain Doppler spectrum signals as the result of the analysis. To be specific, with short-time Fourier transform (STFT), the FFT calculator 11 multiplies the Doppler signals (IQ signals) represented with the time axis by the window function, thereby converting them into signals represented with the frequency axis (Doppler spectrum signals). The Doppler spectrum signals outputted from the FFT calculator 11 are stored into the Doppler waveform memory 12.

The display controller 15 controls the display 17 to display the Doppler spectrum image obtained by the FFT calculator 11. To be specific, the display controller 15 controls the display 17 to display the Doppler spectrum image with the vertical axis taking transmission frequency f (velocity v) and the horizontal axis taking time t.

Further, when the operator gives an instruction of standstill display by using the input part 18, the display controller 15 receives the instruction of standstill display from the user interface (UI) 16.

Then, at the timing of the instruction of standstill display, the display controller 15 controls the display 17 to display the Doppler spectrum image displayed on the display 17 at standstill. In other words, the display controller 15 controls the display 17 to display a Doppler spectrum image acquired at a certain time. In this state, the display controller 15 controls the display 17 to display an ROI marker for designating a region of interest (ROI), in a superimposed state on the Doppler spectrum image. In one example, the display controller 15 controls the display 17 to display an ROI marker, which encircles a certain area, for designating a desired Doppler velocity range and a desired time frame, in the superimposed state on the Doppler spectrum image. The operator can move the ROI marker to a desired position on the Doppler spectrum image by using the input part 18. The operator can designate a Doppler velocity range and time frame desired to observe, with this ROI marker.

Figure 3A:
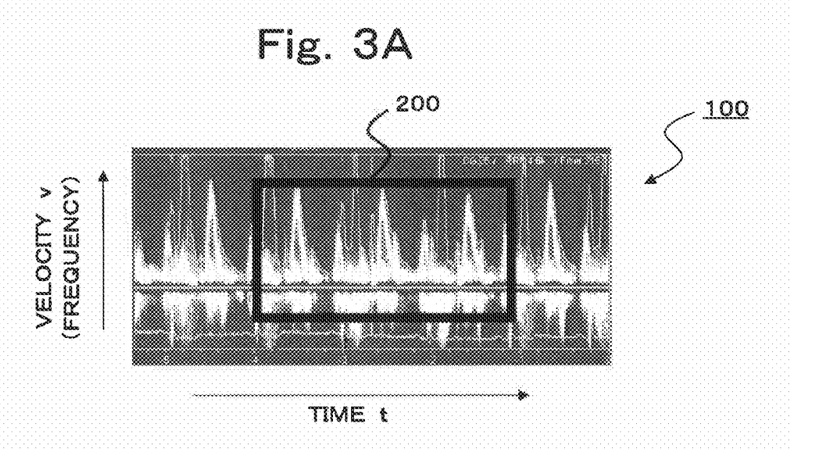
FIG. 3A is a view showing a screen on which a Doppler spectrum image is displayed.

Here, a Doppler spectrum image displayed on the display 17 will be described with reference to FIGS. 3A, 3B and 3C. FIG. 3A is a view showing a screen on which a Doppler spectrum image is displayed.

Figure 3B:
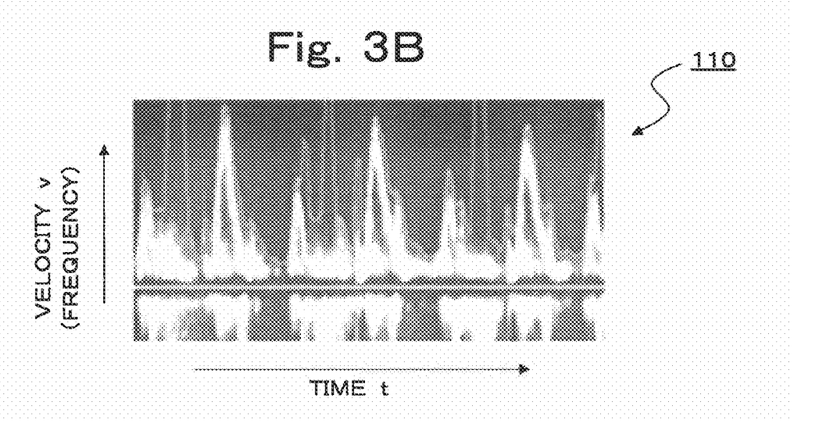
FIG. 3B is a view showing a screen on which a magnified Doppler spectrum image is displayed.

FIG. 3B is a view showing a screen on which a magnified Doppler spectrum image is displayed. FIG. 3C is a view showing a screen on which a Doppler spectrum image generated through a resampling process is displayed.

As shown in FIG. 3A, the display controller 15 controls the display 17 to display a Doppler spectrum image 100 with the vertical axis taking velocity v (frequency) and the horizontal axis taking time t.

Moreover, the display controller 15 controls the display 17 to display an ROI marker 200 encircling a certain area, in a superimposed state on the Doppler spectrum image 100. In this embodiment, the display controller 15 generates the marker 200 encircling a rectangular area, and controls the display 17 to display the marker so as to be superimposed on the Doppler spectrum image 100.

While observing the Doppler spectrum image 100 displayed on the display 17, the operator moves the ROI marker 200 on the Doppler spectrum image 100 by using the input part 18, and designates a desired Doppler velocity range and time frame. In accordance with the moving instruction inputted from the input part 18, the display controller 15 moves the ROI marker 200 on the Doppler spectrum image 100 and controls the display 17 to display it. For example, by using the input part 18, the operator changes the width of the ROI marker 200 in the vertical axis direction (Doppler velocity range direction), the width of the ROI marker 200 in the horizontal axis direction (time axis direction) or its position on the Doppler spectrum image 100, thereby designating a desired Doppler velocity range and a desired time frame. Moreover, the operator designates a desired velocity offset (BLS) by using the input part 18.

Information indicating the desired Doppler velocity range and desired time frame designated by the operator is outputted from the user interface 16 to the display controller 15. The display controller 15 reads a Doppler spectrum image acquired in the designated time frame from the Doppler waveform memory 12, and controls the display 17 to display the Doppler spectrum image magnified or reduced in accordance with the designated Doppler velocity range. For example, it is possible to display a magnified Doppler spectrum image by decreasing the Doppler velocity range. It is also possible to display a reduced Doppler spectrum image by increasing the Doppler velocity range.

For example, as shown in FIG. 3A, when the Doppler velocity range is too large, the scale of the screen is large, and therefore, the Doppler spectrum image is displayed small. In this case, as shown in FIG. 3A, part of the Doppler spectrum image 100 is designated by the ROI marker 200. The display controller 15, as shown in FIG. 3B, reads out a Doppler spectrum image 110 contained in the area designated by the ROI marker 200 from the Doppler waveform memory 12 and controls the display 17 to display it. Consequently, part of the Doppler spectrum image 100 is magnified and displayed. In other words, when a smaller Doppler velocity range is designated by the ROI marker 200, a Doppler spectrum image falling within the Doppler velocity range is displayed. At this stage, the Doppler spectrum image 110 is a simply magnified image (digitally zoomed image) of the Doppler spectrum image 100, so the image quality per pixel on the screen is deteriorated.

Besides, when the operator adjusts the velocity offset (BLS) by using the input part 18, the display controller 15 controls to display a Doppler spectrum image at a desired position of the Doppler velocity range (vertical axis), in accordance with the velocity offset (BLS).

Figure 4A:
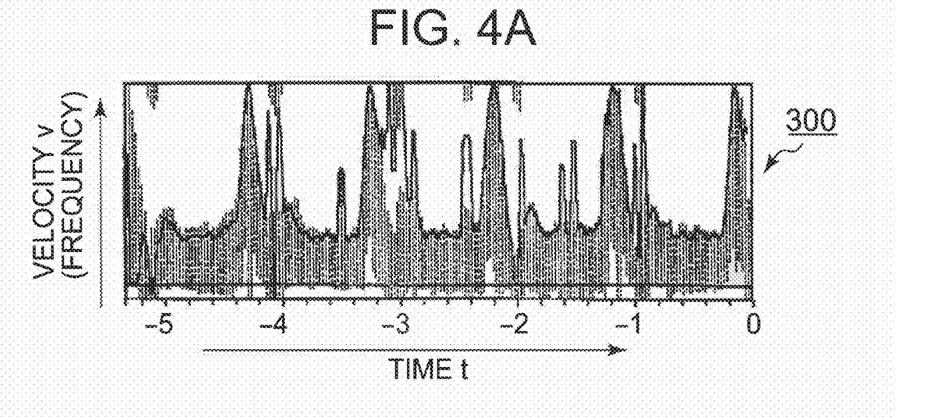
FIG. 4A is a view showing a screen on which a Doppler spectrum image is displayed.
Figure 4B:
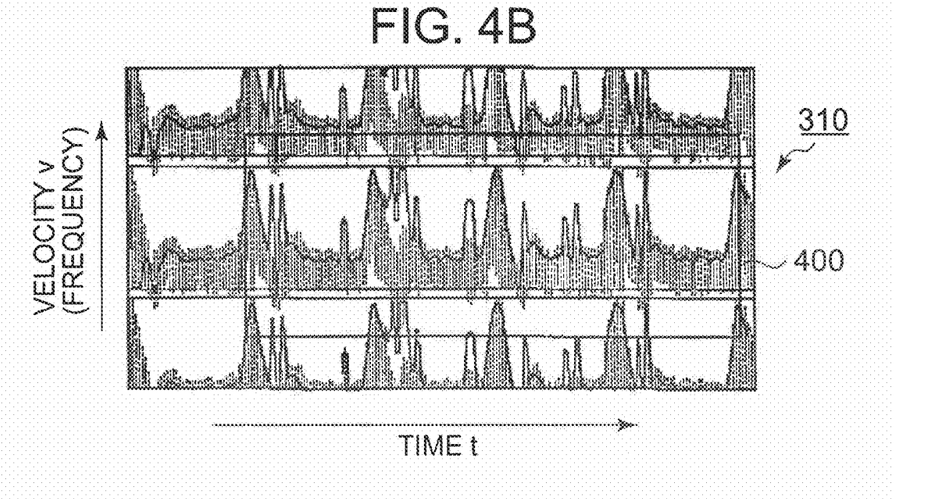
FIG. 4B is a view showing a screen on which a reduced Doppler spectrum image is displayed.
Figure 4C:
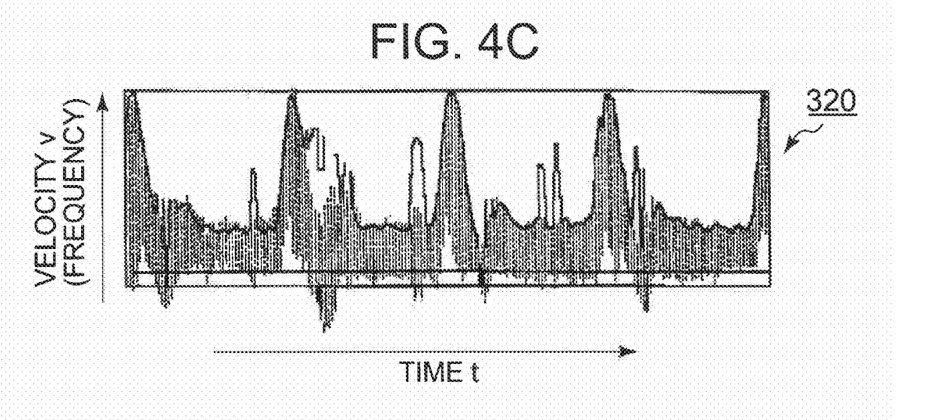
FIG. 4C is a view showing a screen on which a Doppler spectrum image generated through a resampling process is displayed.

Another example of a Doppler spectrum image will be described with reference to FIGS. 4A, 4B and 4C. FIG. 4A is a view showing a screen on which a Doppler spectrum image is displayed. FIG. 4B is a view showing a screen on which a reduced Doppler spectrum image is displayed. FIG. 4C is a view showing a screen on which a Doppler spectrum image generated through a resampling process is displayed.

For example, when the Doppler velocity range is too small, a phenomenon of aliasing (folding) occurs in a Doppler spectrum image 300 and is displayed on the display 17 as shown in FIG. 4A. In this case, as shown in FIG. 4B, the display controller 15 increases the Doppler velocity range and controls the display 17 to display a Doppler spectrum image 310. Consequently, the Doppler spectrum image 300 is reduced and displayed. Moreover, the display controller 15 controls the display 17 to display an ROI marker 400 in the superimposed state on the Doppler spectrum image 310. When part of the Doppler spectrum image 310 is designated by the ROI marker 400, the display controller reads out a Doppler spectrum image contained in the area designated by the ROI marker 400 from the Doppler waveform memory and controls the display 17 to display it. Consequently, part of the Doppler spectrum image 310 is magnified and displayed. At this stage, the magnified Doppler spectrum image is a simply magnified image (digital-zoomed image), so the image quality per pixel on the screen is deteriorated. Besides, when the operator adjusts the velocity offset (BLS) by using the input part 18, the display controller 15 controls to display a Doppler spectrum image at a desired position of the Doppler velocity range (vertical axis) in accordance with the velocity offset (BLS).

Then, the operator adjusts the time frame, Doppler velocity range, and velocity offset (BLS) by using the input part 18 so that a Doppler spectrum image acquired in a desired time frame falls within a desired Doppler velocity range and is displayed on the display 17.

Information indicating the time frame, Doppler velocity range, and velocity offset (BLS) designated by using the input part 18 is outputted from the user interface (UI) 16 to the Doppler processor 4.

In accordance with a sampling frequency corresponding to the Doppler velocity range designated by the operator, the processor 9 reads out IQ signals acquired in the time frame designated by the operator from the first memory 8 and executes a resampling process.

The processor 9 executes the resampling process at a sampling frequency obtained by multiplying the sampling frequency equivalent to the pulse repetition frequency (PRF) by a rational number, in accordance with the Doppler velocity range designated by the operator.

To be specific, by using an interpolator and a decimator, the processor 9 executes the resampling process at a sampling frequency obtained by multiplying the sampling frequency equivalent to the pulse repetition frequency (PRF) by a rational number.

The processor 9 is shown in FIG. 2. As shown in FIG. 2, the processor 9 includes an upsampling part 91, a Complex Band Pass Filter (CBPF) 92, a Complex Band Pass Filter 93, a setting part 94, a synthesizer 95, and a downsampling part 96. The upsampling part 91 is composed of circuits for two channels for real-part components and imaginary-part components, to which Doppler signals (IQ signals) of complex number signals are inputted. The CBPF 92 is assigned to the side of positive-side frequency components (the side of forward components) of the Doppler signals (IQ signals). The CBPF 93 is assigned to the side of negative-side frequency components (the side of reverse components) of the Doppler signals (IQ signals).

For example, in the case of resampling at a sampling frequency fs' corresponding to the Doppler velocity range designated by the operator, the sampling frequency fs' is defined by Equation (1):

$$fs' = (N2/N1) \times fs \qquad \text{(Equation (1))},$$

where fs is a sampling frequency (equivalent to the pulse repetition frequency (PRF)), and N1 and N2 are integers.

As shown in Equation (1), the sampling frequency fs' is defined by multiplying the sampling frequency fs by a rational number.

The upsampling part 91 inserts a zero (0) value to between the signal values of inputted Doppler signals (IQ signals), thereby increasing the sampling frequency of the output value. This process is executed for each of the real-part channel and imaginary-part channel so that the length of the Doppler signals in the time-series direction gets multiplied by an integral number N2 (N2=2, 3, . . . ) by the zero insertion. To be specific, the sampling frequency of the output value is increased N2 times by inserting (N2−1) pieces of zero (0) values to between the signal values of the Doppler signals. However, in order to remove spectral components newly generated by upsampling when the nyquist frequency is increased N2 times, a digital low pass filter process is executed on the signals after upsampling. This digital low pass filter process is executed by the CBPF 92 and CBPF 93.

The Doppler signals having been subjected to the zero insertion are transmitted to the CBPF 92 and the CBPF 93, respectively, and are subjected to the band pass filtering process. When the band pass filtering is executed, the coefficient in each of the CBPF 92 and the CBPF 93 is controlled in accordance with the baseline shift (BLS).

Information regarding the shift (BLS) is outputted from the user interface (UI) 16 to the processor 9.

The CBPF 92 and CBPF 93 with the coefficients having been controlled executes filtering on the Doppler signals (IQ signals). First, the operator operates the input part 18 in a state where a Doppler spectrum image is displayed on the display 17, whereby a baseline BL of the Doppler spectrum image is shifted. Information on the shift (BLS) is outputted from the user interface (UI) 16 to the processor 9.

The setting part 94 then sets the bandwidth and center frequency of the CBPF 92 and CBPF 93, based on the baseline shift (BLS) outputted from the user interface (UI) 16, for example, by the method described in Japanese Unexamined Patent Application Publication JP-A 2002-325767. This setting is executed so as to correspond to the multiple N2 of the zero insertion by the upsampling part 91 and the multiple 1/N1 by the downsampling part 96.

Here, a filtering coefficient Z' and a cutoff frequency fc (fwd) at the CBPF 92 assigned to the side of the positive-side frequency components (the side of Forward components) of the Doppler signals (IQ signals) are given by the following Equations (2) and (3):

Filtering coefficient $Z'=\exp(-j\pi \times (BLS/2))$ (Equation (2));

and

Cutoff frequency $fc(fwd)=(N2/N1) \times fs \times (0.5+BLS)$ (Equation (3)).

Further, a filtering coefficient Z" and a cutoff frequency fc (rev) at the CBPF 93 assigned to the side of the negative-side frequency components (the side of Reverse components) of the Doppler signals (IQ signals) are given by the following Equations (4) and (5):

Filtering coefficient $Z''=\exp(-j\pi \times (0.5-BLS)/2)$ (Equation (4)); and

Cutoff frequency $fc(rev)=(N2/N1) \times fs \times (BLS-0.5)$ (Equation (5)).

The CBPF 92 and the CBPF 93 execute filtering on the Doppler signals (IQ signals) at the filtering coefficients and cutoff frequencies described above.

The synthesizer 95 synthesizes the positive-side frequency components of the Doppler signals outputted from the CBPF 92 and the negative-side frequency components of the Doppler signals outputted from the CBPF 93, and outputs to the downsampling part 96.

The downsampling part 96 multiplies the sampling frequency of the inputted Doppler signals (IQ signals) by 1/N1. The downsampling part 96 reduces the sampling frequency of the output signals by picking up the inputted Doppler signals at the intervals of N1. However, because the nyquist frequency is halved after downsampling, folding aliasing components may be superimposed on the Doppler signal components. Therefore, high-frequency components equal to or more than the nyquist frequency are eliminated by digital low pass filtering before downsampling. This digital low pass filtering is executed by the CBPF 92 and the CBPF 93. The IQ signals after the sampling process outputted from the processor 9 are stored into the second memory 10.

For example, in the case of displaying a Doppler spectrum image at standstill by magnifying, the Doppler velocity range is decreased. For example, in the case of decreasing the Doppler velocity range to 2/3, the upsampling part 91 executes upsampling with N2=2, and the downsampling part 96 executes downsampling with N1=3. On the contrary, in the case of displaying the Doppler spectrum image by reducing, the Doppler velocity range is increased. For example, in the case of increasing the Doppler velocity range to 3/2, the upsampling part 91 executes upsampling with N2=3, and the downsampling part 96 executes downsampling with N1=2. Thus, the processor 9 executes the resampling process at a sampling frequency obtained by multiplying the pulse repetition frequency PRF by a rational number.

In a case where the Doppler velocity range is increased, the folding phenomenon may occur at the time of processing at the sampling frequency fs' even if the folding phenomenon does not occur at the time of processing at the initial sampling frequency fs. In this case, the CBPF 92 and the CBPF 93 after upsampling need precipitous band limit. For example, there is a need to eliminate frequency components of fs'/2 or more.

In the case of decreasing the Doppler velocity range when $2 \times fs \le fs' < 4 \times fs$, the processor 9 executes a homomorphic analysis. For example, a function antialias (f) is defined for the process by the processor 9 and the process is executed as fs"=antialias (fs').

The FFT calculator 11 reads out the IQ signals after resampling from the second memory 10, applies a short-time Fourier transform (STFT), and multiplies Doppler signals represented with the time axis (IQ signals) by a window function to convert them into signals represented with the frequency axis (Doppler spectrum signals). At this moment, in accordance with a change in Doppler velocity range (sampling frequency) designated by the operator, the FFT calculator 11 adjusts the frequency resolution and the temporal resolution and generates Doppler spectrum signals by, for example, a method described in Japanese Unexamined Patent Application Publication JP-A 11-285495. Here, this process will be briefly described.

A temporal resolution $\Delta X$ and a frequency resolution $\Delta Y$ are given by the following Equations (6) and (7):

$\Delta X = (Dx \times N \times K \times M)/(PRF \times S)$ (Equation (6)); and $\Delta Y = Dy/(N \times Ww)$ (Equation (7)), where:

Dx is the number of pixels of the Doppler spectrum image in the horizontal axis (time axis) of the display range;
Dy is the number of pixels of the Doppler spectrum image in the vertical axis (frequency axis) of the display range;
N is the FFT data number;
K is the parameter in alternate scan (the number of scanning lines repeatedly scanned sequentially in alternate scan);
M is the decimation ratio;
PRF is the pulse repetition frequency (equivalent to Doppler velocity range);
S is the scroll velocity; and
Ww is the window weight.

The alternate scan is a scan such that a scanning line is changed for every transmission/reception of ultrasonic waves, and after transmission/reception of ultrasonic waves on a specified number of scanning lines, transmission/reception of ultrasonic waves is started from the first scanning line again.

Although there is a limit that the FFT data number N is a power of two, a calculatory data number for achieving an intended frequency resolution is not a power of two in many cases. Therefore, a number equal to or more than the calculatory data number, which is a power of two closest to the number, is selected as the FFT data number N.

Mismatch between the selected FFT data number N and the calculatory data number is resolved by multiplying by the FFT window function. The parameter that determines the size of this window (window width) is a window weight Ww. For example, in a case where the calculatory data number is 320, 512 is selected as the FFT data number N, and in this case, the window weight Ww is set to 5/8. For example, for keeping the ratio of the frequency resolution to the temporal resolution constant, when the pulse repetition frequency PRF (Doppler velocity range), the scroll velocity S, the parameter K, the decimation ratio M, and Dy are given, the FFT calculator 11 calculates the FFT data number N and the window weight Ww (window width) for keeping a desired ratio. In other words, when the pulse repetition frequency PRF (Doppler velocity range) is changed (when the temporal resolution is changed), the FFT calculator 11 accordingly adjusts the FFT data number (A4) and changes the frequency resolution to keep the ratio of the frequency resolution to the temporal resolution constant.

The data number (A4) is not necessarily a power of two that can be handled by FFT as described above. Therefore, a number equal to or more than the calculatory data number (A4), which is a power of two closest to the number, is selected, and the selected FFT data number N and the window weight Ww for making up the mismatch therebetween are selected. By such process, it is possible to keep the ratio of the frequency resolution ΔY to the temporal resolution ΔX constant even if the Doppler velocity range is changed.

Further, it is also possible to execute a process to fix the temporal resolution at a constant value desired by the operator even if the frequency resolution varies. For example, when the data number N is changed, the FFT calculator 11 changes at least one of the parameters other than the data number N in the above Equation (6) and keeps the temporal resolution at a constant value. Alternatively, it is possible to execute a process to fix the frequency resolution at a constant value desired by the operator even if the temporal resolution varies.

The Doppler spectrum signal with the Doppler velocity range and velocity offset changed is outputted from the FFT calculator 11 to the Doppler waveform memory 12, and is stored into the Doppler waveform memory 12. The display controller 15 then reads out the Doppler spectrum image in which the Doppler velocity range, etc. have been changed from the Doppler waveform memory 12, and controls the display 17 to display it.

Figure 3C:
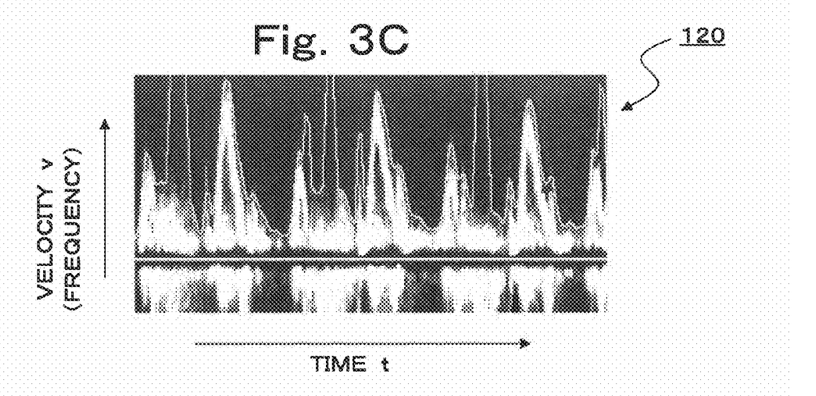
FIG. 3C is a view showing a screen on which a Doppler spectrum image generated through a resampling process is displayed.

Here, examples of a newly generated Doppler spectrum image are shown in FIGS. 3C and 4C. For example, the Doppler spectrum image 120 shown in FIG. 3C is an image obtained by changing the Doppler velocity range and velocity offset, applying the resampling process by the processor 9, and applying the STFT process by the FFT calculator 11. The Doppler spectrum image 110 shown in FIG. 3B is an image that the Doppler spectrum image 100 is simply magnified and displayed. Since the Doppler spectrum image 110 is a simple digitally zoomed image, the image quality per pixel on the screen is deteriorated.

On the other hand, in the Doppler spectrum image 120 obtained by applying the resampling process and the STFT process, the temporal resolution and frequency resolution are not deteriorated. Thus, according to the ultrasonic imaging apparatus 1 of this embodiment, it is possible to generate the Doppler spectrum image 120 represented by a desired Doppler velocity range and velocity offset without deteriorating the temporal resolution or frequency resolution.

Further, the Doppler spectrum image 320 shown in FIG. 4C is also an image obtained by changing the Doppler velocity range and velocity offset, applying the resampling process by the processor 9, and applying the STFT process by the FFT calculator 11. This Doppler spectrum image 320 is also generated without deterioration of the temporal resolution and frequency resolution.

When a desired Doppler velocity range (PRF) and velocity offset (BLS) are determined by the operator, information indicating the Doppler velocity range (PRF) is outputted from the user interface (UI) 16 to the transceiver 3, and information indicating the velocity offset (BLS) is outputted from the user interface (UI) 16 to the FFT calculator 11. When receiving the Doppler velocity range (PRF) outputted from the user interface (UI) 16, the transceiver 3 causes the ultrasonic probe 2 to transmit/receive ultrasonic waves in accordance with the Doppler velocity range (PRF). Moreover, when receiving the velocity offset (BLS) from the user interface (UI) 16, the FFT calculator 11 changes the read-out address of the FFT process by the shift amount to adjust the offset of the velocity. Thus, when the Doppler velocity range and velocity offset are changed, scan is executed in accordance with the changed Doppler velocity range, and the FFT process is executed based on the changed velocity offset.

The user interface (UI) 16 includes the display 17 and the input part 18. The display 17 is composed of a monitor such as a CRT and a liquid crystal display, and displays an image such as a tomographic image, a 3-dimensional image and a Doppler spectrum image on its screen. The input part 18 is composed of a keyboard, a mouse, a trackball, a TCS (Touch Command Screen), or the like. The operator can move the ROI marker to a desired position on the screen of the display 17 by using the input part 18.

The input part 18 may be provided with a switch for changing the size and position of the ROI marker. For example, the input part 18 may be provided with a switch A for instructing increase or decrease of the ROI marker in the longitudinal direction (Doppler velocity range), and a switch B for instructing increase or decrease of the ROI marker in the lateral direction (time axis). Moreover, the input part 18 may be configured so as to change the position of the ROI marker by the trackball disposed to the input part 18 and select a time phase to observe. The operator moves the ROI marker to a desired position and changes the size of the ROI marker to a desired size by using the switch A, the switch B and the trackball in a state where the Doppler spectrum image is at standstill. Consequently, it is possible to designate a desired Doppler velocity range and a desired time frame.

Further, the ultrasonic imaging apparatus 1 is provided with a controller (not shown). The controller is connected to the transceiver 3, the Doppler processor 4, the B-mode processor 13, the DSC 14, the display controller 15, and the user interface (UI) 16. The controller controls the operation of each of the parts.

The display controller 15 may be configured not to control the display 17 to display a Doppler spectrum image simply magnified or reduced in accordance with an instruction by the operator. Also in this case, similarly in the embodiment described above, at a sampling frequency corresponding to the Doppler velocity range designated by the operator, the processor 9 reads out the IQ signals acquired in a time frame designated by the operator from the first memory 8 and executes the resampling process. Then, the FFT calculator 11 applies short-time Fourier transform (STFT) to the IQ signals after the resampling, thereby generating a new Doppler spectrum image. The display controller 15 controls the display 17 to display the new Doppler spectrum image.

Consequently, when the operator designates a desired Doppler velocity range and time frame by using the ROI marker, a new Doppler spectrum image is displayed on the display 17 while a simply magnified or reduced Doppler spectrum image is not displayed on the display 17. Since a simply magnified or reduced Doppler spectrum image is not generated, it is possible to save a time required for generation thereof. As a result, it becomes possible to shorten a time period between designation of the Doppler velocity range and time frame and display of a new Doppler spectrum image. In other words, it becomes possible to display a new Doppler spectrum image more quickly.

For example, the display controller 15 may be configured not to control the display 17 to display the Doppler spectrum image 110 (image shown in FIG. 3B), which is a simply magnified image (a digitally zoomed image) of the Doppler spectrum image 100. Also in this case, the processor 9 executes the resampling process and the FFT calculator 11 applies short-time Fourier transform (STFT) to the IQ signals after the resampling, thereby generating a new Doppler spectrum image. Then, as shown in FIG. 3C, the display controller 15 controls the display 17 to display the new Doppler spectrum image 120.

Thus, only the Doppler spectrum image 120 generated through the resampling process is displayed, while the digitally zoomed Doppler spectrum image 110 is not displayed. Consequently, it is possible to shorten a time period between designation of the Doppler velocity range and time frame and display of the new Doppler spectrum image 120.

Figure 6:
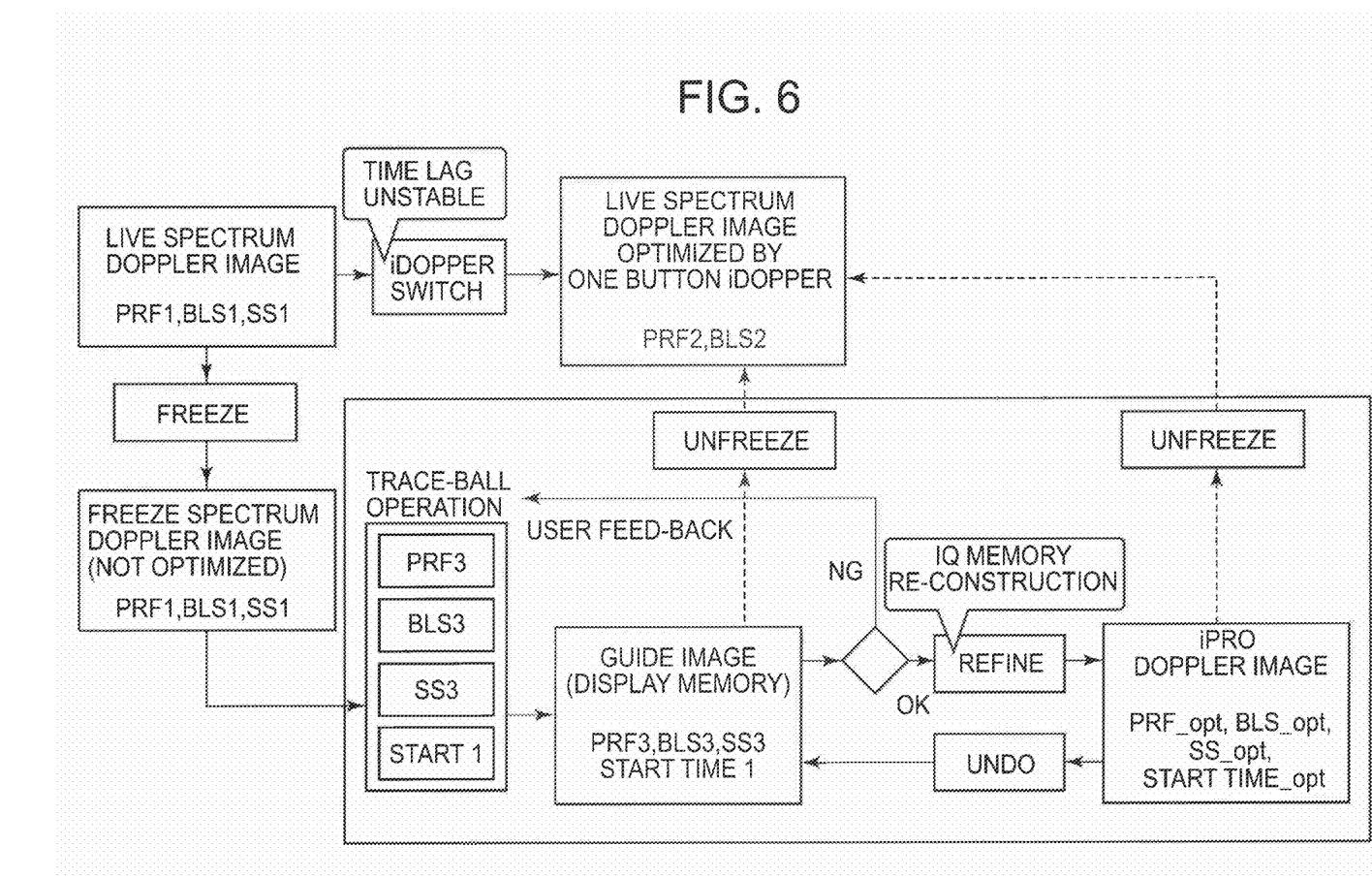
FIG. 6 is a view for explaining a process of reconstructing IQ data before execution of the FFT process and executing frequency analysis with a different parameter.
Figure 7:
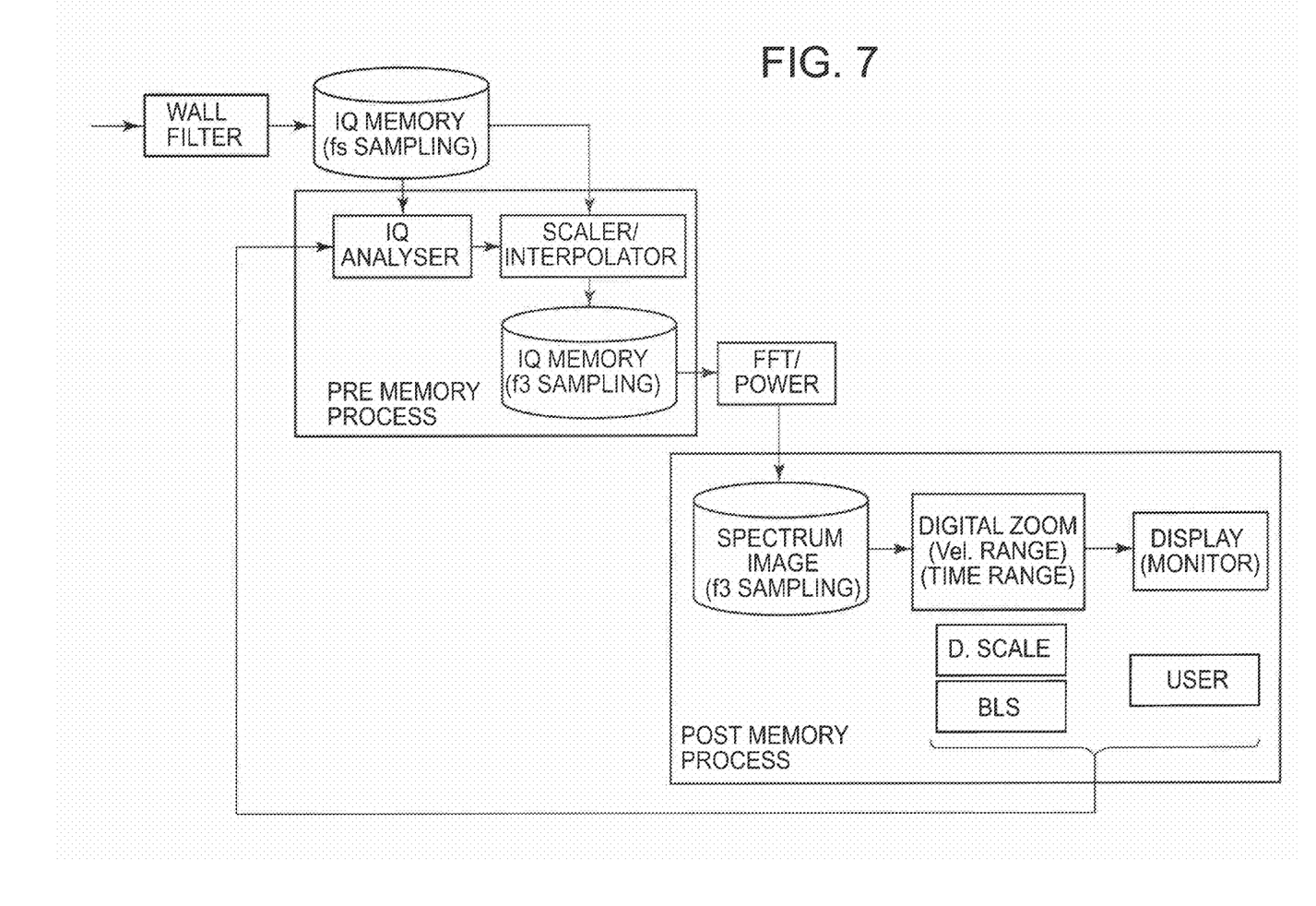
FIG. 7 is a view showing a system that performs acquisition of IQ data and reconstruction of IQ data.

A specific example of the aforementioned embodiment is shown in FIGS. 6 and 7. FIG. 6 shows an example of a process of reconstructing IQ data before execution of the FFT process and executing frequency analysis by FFT with a different parameter.

Moreover, FIG. 7 shows an example of a system that performs acquisition of IQ data and reconstruction of IQ data.

(Ultrasonic Image Processing Apparatus)

Further, an ultrasonic image processing apparatus may be composed of the aforementioned Doppler processor 4, display controller 15, and user interface (UI) 16. The ultrasonic image processing apparatus executes the resampling process at a sampling frequency corresponding to a desired Doppler velocity range designated by the operator, and further executes the STFT process on the received signals, thereby generating a Doppler spectrum image represented in the Doppler velocity range.

(Operations)

Figure 5:
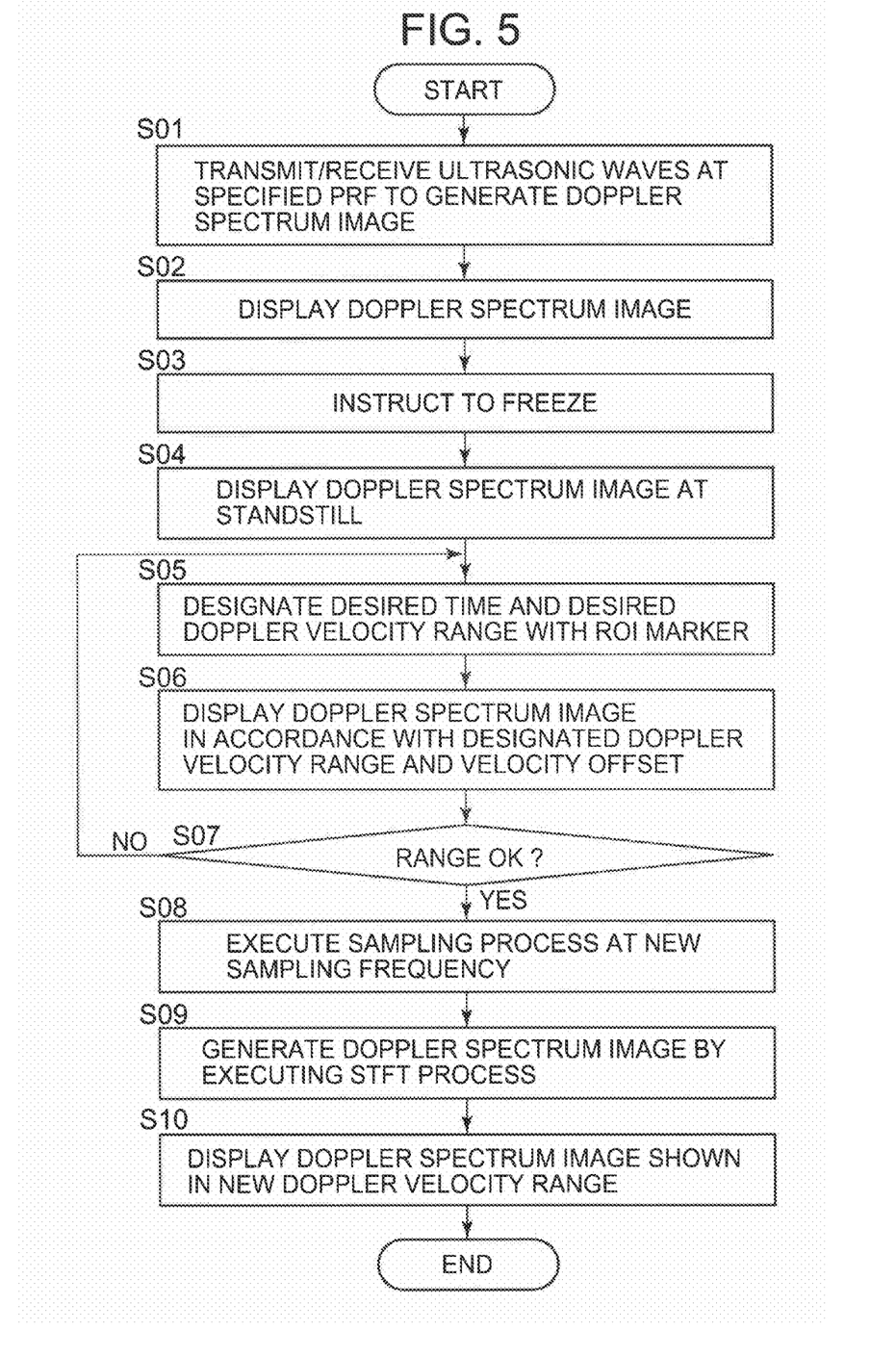
FIG. 5 is a flow chart showing a series of operations by the ultrasonic imaging apparatus according to the embodiment of the present invention.

Next, a series of operations of the ultrasonic imaging apparatus according to the embodiment of the present invention will be described with reference to FIG. 5. FIG. 5 is a flow chart showing the series of operations of the ultrasonic imaging apparatus according to the embodiment of the present invention.

(Step S01)

First, with the ultrasonic probe 2 and the transceiver 3, ultrasonic waves are transmitted to a subject at a specified pulse repetition frequency (PRF) having been set initially, and reflected waves from the subject are received. The received signals received by the transceiver 3 are processed by the quadrature detector 5, the range gate processor 6, and the wall filter 7. Then, Doppler signals (IQ signals) are sequentially stored into the first memory 8. The FFT calculator 11 sequentially generates Doppler spectrum images by executing frequency analysis on the Doppler signals. The Doppler spectrum images generated by the FFT calculator 11 are sequentially stored into the Doppler waveform memory 12.

(Step S02)

The display controller 15 reads out a Doppler spectrum image from the Doppler waveform memory 12 and controls the display 17 to display the Doppler spectrum image with the vertical axis taking transmission frequency f (velocity v) and the horizontal axis taking time t.

(Step S03)

Then, while observing the Doppler spectrum image displayed on the display 17, the operator issues an instruction to display the image at standstill, at a desired timing by using the input part 18.

(Step S04)

The display controller 15 receives the instruction of standstill display from the user interface (UI) 16, and at the timing of issue of the instruction, the display controller 15 makes the Doppler spectrum image displayed in the display 17 stand still, and controls the display 17 to display it.

(Step S05)

Furthermore, the display controller 15 controls the display 17 to display the ROI marker encircling a certain area in the superimposed state on the Doppler spectrum image. For example, as shown in FIG. 3A, the display controller 15 controls the display 17 to display the Doppler spectrum image 100 in the fixed state, and controls to display the ROI marker 200 so as to be superimposed on the Doppler spectrum image 100. Then, the operator designates a desired Doppler velocity range and a desired time frame by changing the width of the ROI marker 200 in the vertical axis direction (Doppler velocity range direction), the width thereof in the horizontal axis direction (time axis direction), or the position thereof by using the input part 18 while observing the Doppler spectrum image 100 displayed on the display 17. Further, the operator designates a desired velocity offset (BLS) by using the input part 18. Thus, the operator designates the Doppler velocity range and time frame desired to observe, by using the ROI marker.

(Step S06)

The display controller 15 reads, from the Doppler waveform memory 12, a Doppler spectrum image acquired in the time frame designated with the ROI marker 200, and controls the display 17 to display a Doppler spectrum image magnified or reduced in accordance with the designated Doppler velocity range. For example, when part of the Doppler spectrum image 100 is designated with the ROI marker 200 as shown in FIG. 3A, the display controller 15 reads out the Doppler spectrum image 110 included in the area designated with the ROI marker 200 from the Doppler waveform memory 12, and controls the display 17 to display it as shown in FIG. 3B. Consequently, part of the Doppler spectrum image 100 is magnified and displayed. In this stage, the Doppler spectrum image 110 is a simply magnified image (digitally zoomed image) of the Doppler spectrum image 100, so the image quality per pixel on the screen is deteriorated.

(Step S07)

Then, the operator observes the displayed Doppler spectrum image having been magnified or reduced, and checks whether the Doppler spectrum image is displayed within the Doppler velocity range.

Moreover, it is checked whether the velocity offset of the displayed Doppler spectrum image is a proper value. In other words, it is checked whether the Doppler velocity range is not too small or too large for the Doppler spectrum image desired to observe. In a case where the displayed Doppler spectrum image having been magnified or reduced is not displayed within the Doppler velocity range, or in a case where the velocity offset is not a proper value (Step S07, No), the operator designates a desired Doppler velocity range and a desired time frame with the ROI marker (Step S05). Consequently, the Doppler spectrum image is displayed in accordance with the designated Doppler velocity range (Step S06). In other words, when the Doppler velocity range is too small or too large for the Doppler spectrum image desired to observe, the operator designates a desired Doppler velocity range with the ROI marker again.

Meanwhile, in a case where the displayed Doppler spectrum image having been magnified or reduced is within the Doppler velocity range and the velocity offset is a proper value (Step S07, Yes), the operator gives an instruction to reprocess by using the input part 18.

Consequently, information indicating the desired Doppler velocity range and velocity offset given by the operator is outputted from the user interface (UI) 16 to the processor 9.

(Step S08)

The processor 9 reads out the Doppler signals (IQ signals) from the first memory 8, and executes the resampling process at a sampling frequency obtained by multiplying the sampling frequency equivalent to the pulse repetition frequency (PRF) by an integral number in accordance with the designated Doppler velocity range. To be specific, the processor 9 executes upsampling, filtering by a Complex Band Pass Filter, and downsampling on the read-out Doppler signals.

(Step S09)

The FFT calculator 11 applies the STFT process to the Doppler signals having been subjected to the resampling process at the new sampling frequency, thereby generating new Doppler spectrum signals.

These Doppler spectrum signals are stored into the Doppler waveform memory 12.

(Step S10)

Then, the display controller 15 reads a new Doppler spectrum image from the Doppler waveform memory 12, and controls the display 17 to display it. Consequently, it is possible to display the new Doppler spectrum image 120 without deteriorating the temporal resolution and frequency resolution, for example, as shown in FIG. 3C.

As described above, according to the ultrasonic imaging apparatus 1 of this embodiment, it is possible to easily set a Doppler velocity range and velocity offset suitable for display of a Doppler spectrum image, by changing the Doppler velocity range and velocity offset while observing a Doppler spectrum image at standstill. In other words, since it is possible to check a desired Doppler velocity range and velocity offset by displaying a Doppler spectrum image at standstill in the magnified or reduced state, it is possible to easily set the desired Doppler velocity range and velocity offset.

Then, it becomes possible to, based on the set Doppler velocity range and velocity offset, execute the resampling process on the Doppler signals (IQ signals) before the FFT process, and further apply the STFT process thereon, thereby generating and displaying a Doppler spectrum image represented in a desired Doppler velocity range without deteriorating the temporal resolution and frequency resolution.

In other words, it is possible to obtain a Doppler spectrum image represented in a desired Doppler velocity range without deteriorating the temporal resolution and frequency resolution by not only simply magnifying or reducing the Doppler spectrum image in accordance with the Doppler velocity range but also executing the resampling process and STFT process again based on the set Doppler velocity range. Thus, since it is possible to obtain a Doppler spectrum image represented in a desired Doppler velocity range without deteriorating the image quality, it becomes possible to execute more accurate measurement based on the Doppler spectrum image.

Further, the ultrasonic imaging apparatus 1 according to this embodiment generates a new Doppler spectrum image by reprocessing a Doppler spectrum image acquired in a time frame desired to measure, in accordance with a desired Doppler velocity range and velocity offset.

It is therefore possible to perform a desired measurement based on the new Doppler spectrum image in the time frame desired to measure.

Meanwhile, in the conventional technique, the current and later Doppler velocity range is estimated based on Doppler spectrum images acquired in the past. Therefore, when variations occur after the estimation, it is necessary to execute the estimation process again, so that it is difficult to perform stable measurements. On the contrary, according to the ultrasonic imaging apparatus 1 of this embodiment, it is not necessary to execute the estimation process based on past Doppler spectrum images, and therefore, it becomes possible to execute stable measurements with a Doppler spectrum image.

Besides, when a desired Doppler velocity range and velocity offset are determined, the transceiver 3 causes the ultrasonic probe 2 to transmit ultrasonic waves in accordance with the Doppler velocity range (PRF). Moreover, in accordance with the velocity offset (BLS), the FFT calculator 11 changes the read-out address of the FFT process by shift amount, and adjusts the offset of the velocity. Consequently, the Doppler velocity range (PRF) and the velocity offset (BLS) are updated.

What is claimed is:

1. An ultrasonic imaging apparatus, comprising:
    a scanner configured to transmit and receive ultrasonic waves to and from a diagnosis site including a moving fluid in a subject at a preset pulse repetition frequency (PRF);
    a storage configured to store first IQ signals acquired by the scanner;
    Doppler processing circuitry configured to generate a Doppler spectrum image by executing frequency analysis to the first IQ signals, the vertical and horizontal axes of the Doppler spectrum image corresponding to velocity and time;
    a display configured to display the Doppler spectrum image as a still image; and
    a user interface configured to set a Region Of Interest (ROI) having a rectangle shape on the Doppler spectrum image, and determine a velocity range, a velocity offset, and a period based on position and size of the ROI; wherein
    the Doppler processing circuitry configured to:
        determine a sampling frequency based on the velocity range input from the user interface,
        read out, from the storage, only a part of the first IQ signals corresponding to the period,
        execute a resampling process on the part of the first IQ signals at the sampling frequency,
        generate second IQ signals by the resampling process, and
        generate a new Doppler spectrum image based on the second IQ signals, the velocity range, and the velocity offset; and
    the display configured to display the new Doppler spectrum image having a size larger than the size of the ROI as a still image, the new Doppler spectrum image being not a real-time image.

2. The ultrasonic imaging apparatus according to claim 1, further comprising:
    a freeze part configured to enter a standstill instruction about the Doppler spectrum image that is a moving image displayed by the display, wherein:
    when the standstill instruction of the Doppler spectrum image is issued from the freeze part, the display is configured to display the Doppler spectrum image as a still image, and displays an ROI marker, which encircles a certain area, for determining the velocity range, the velocity offset, and the period in a superimposed state on the Doppler spectrum image in response to the standstill instruction from the freeze part, and
    the Doppler processing circuitry is configured to execute the resampling process on the part of the first IQ signals, at the sampling frequency based on the velocity range by the ROI marker.

3. The ultrasonic imaging apparatus according to claim 1, wherein:
    the Doppler processing circuitry is configured to execute the resampling process at the sampling frequency obtained by multiplying the preset pulse repetition frequency by a rational number, in accordance with the velocity range.

4. The ultrasonic imaging apparatus according to claim 3, wherein:
the Doppler processing circuitry is configured to execute the resampling process by executing upsampling at the sampling frequency obtained by multiplying the preset pulse repetition frequency by an integral number and then executing downsampling at the sampling frequency obtained by multiplying the preset pulse repetition frequency by an integral number, in accordance with the velocity range.

5. The ultrasonic imaging apparatus according to claim 1, wherein:
the Doppler processing circuitry is configured to generate the new Doppler spectrum image by changing a number of data and a width of a window function in accordance with the velocity range, and to execute the frequency analysis on the first IQ signals having been subjected to the resampling process.

6. The ultrasonic imaging apparatus according to claim 1, wherein the display is further configured to zoom on the Doppler spectrum image on the display, and to overwrite the zoomed on Doppler spectrum image by the new Doppler spectrum image after resampling or regeneration.

7. A method for generating an ultrasonic image, comprising:
transmitting and receiving ultrasonic waves to and from a diagnosis site including a moving fluid in a subject at a preset pulse repetition frequency (PRF);
storing first IQ signals acquired in the transmission and reception into a storage;
generating a Doppler spectrum image by executing frequency analysis to the first IQ signals, the vertical and horizontal axes of the Doppler spectrum image corresponding to velocity and time;
displaying the Doppler spectrum image as a still image at a timing of a standstill instruction from a user interface;
setting a Region Of Interest (ROI) having a rectangle shape on the Doppler spectrum image;
determining a velocity range, a velocity offset, and a period based on position size of the ROI;
determining a sampling frequency based on the velocity range;
reading out, from the storage, only a part of the first IQ signals corresponding to the period;
executing a resampling process on the part of the first IQ signals at the sampling frequency;
generating second IQ signals by the resampling process;
generating a new Doppler spectrum image based on the second IQ signals, the velocity range, and the velocity offset; and
displaying the new Doppler spectrum image having a size larger than the size of the ROI as a still image, the new Doppler spectrum image being not a real-time image.

8. The method for generating an ultrasonic image according to claim 7, further comprising:
entering the standstill instruction about the Doppler spectrum image that is a moving image displayed by the display wherein:
when the standstill instruction of the Doppler spectrum image is issued, displaying the Doppler spectrum image as a still image, and displaying an ROI marker, which encircles a certain range, for determining the velocity range, the velocity offset, and the period in a superimposed state on the Doppler spectrum image in response to the velocity range, the velocity offset, and the period; and
executing the resampling process on the part of the first IQ signals at the sampling frequency based on the velocity range with the ROI marker.

9. The method for generating an ultrasonic image according to claim 7, wherein:
executing the resampling process at the sampling frequency, which is obtained by multiplying the preset pulse repetition frequency by a rational number, in accordance with the velocity range.

10. The method for generating an ultrasonic image according to claim 9, wherein:
executing the resampling process comprises executing upsampling at the sampling frequency and then executing downsampling at the sampling frequency.

11. The method for generating an ultrasonic image according to claim 7, wherein:
generating the new Doppler spectrum image comprises changing a number of data and a width of a window function in accordance with the velocity range and executing the frequency analysis on the first IQ signals having been subjected to the resampling process.

12. The method for generating an ultrasonic image according to claim 7, wherein the Doppler spectrum image on the display is zoomed on after the velocity range is determined on the displayed Doppler spectrum image, and the zoomed on Doppler spectrum image is overwritten by the new Doppler spectrum image after resampling or regeneration.

* * * * *